United States Patent [19]

Bingisser

[11] Patent Number: 5,308,337
[45] Date of Patent: May 3, 1994

[54] MEDICAL TUBE CLIP DEVICE

[76] Inventor: Timothy A. Bingisser, 12431 110th La., NE. #N101, Kirkland, Wash. 98034

[21] Appl. No.: 33,265

[22] Filed: Mar. 16, 1993

[51] Int. Cl.$^5$ ...................... A61M 5/32; A61M 15/08
[52] U.S. Cl. ........................... 604/174; 128/DIG. 26; 128/207.18; 24/346; 24/543; 606/157
[58] Field of Search ....................... 604/174, 177, 178; 128/DIG. 26, 267.18; 24/3 L, 3 M, 327, 331, 346, 339, 347, 482, 543, 487, 490; 606/157

[56] References Cited

U.S. PATENT DOCUMENTS

| | | | |
|---|---|---|---|
| 3,209,755 | 10/1965 | McCarthy et al. | 604/174 |
| 3,990,454 | 11/1976 | Schlesinger | 128/349 R |
| 4,165,748 | 8/1979 | Johnson | 128/348 |
| 4,170,995 | 10/1979 | Levine et al. | 128/346 |
| 4,336,806 | 6/1982 | Eldridge, Jr. | 128/348 |
| 4,382,453 | 5/1983 | Bujan et al. | 24/543 |
| 4,416,038 | 11/1983 | Morrone, III | 24/543 |
| 4,707,906 | 11/1987 | Posey | 24/346 |
| 4,815,175 | 3/1989 | Kasai | 24/543 |
| 4,835,824 | 6/1989 | Durham et al. | 24/346 |
| 4,995,384 | 2/1991 | Keeling | 128/DIG. 26 |
| 5,184,375 | 2/1993 | Hoyt | 24/3 L |

FOREIGN PATENT DOCUMENTS 91322 3/1958 Belgium ............................... 24/487
462593 1/1914 France ............................... 24/487

Primary Examiner—John G. Weiss
Attorney, Agent, or Firm—John R. Flanagan

[57] ABSTRACT

A tube clip device, preferably having a one-piece construction and formed integrally of a resiliently flexible material, includes a flat base member having bar slot and stud slot attachment elements, a flat closure member having bar and stud attachment elements being complementary in shape to and interengageable with the bar slot and stud slot of the base member, a living hinge pivotally connecting the base and closure members together for pivotal movement between opened and closed positions relative to one another, and a clip element mounted on an outer side of the closure member for releasably clasping a flexible medical tube. Upon inserting the base and closure members over an edge of a garment and pivoting the members to the closed position, the bar slot and stud slot of the base member become releasably latched with the bar and stud of the closure member and with the garment edge therebetween, thereby attaching the medical tube clip device to the garment. The clip element mounted on the closure member clasps the medical tube securely for restraining the medical tube from twisting and for dispersing the weight of the medical tube more or less evenly over the garment and upper torso of the person.

17 Claims, 1 Drawing Sheet

U.S. Patent    May 3, 1994    5,308,337
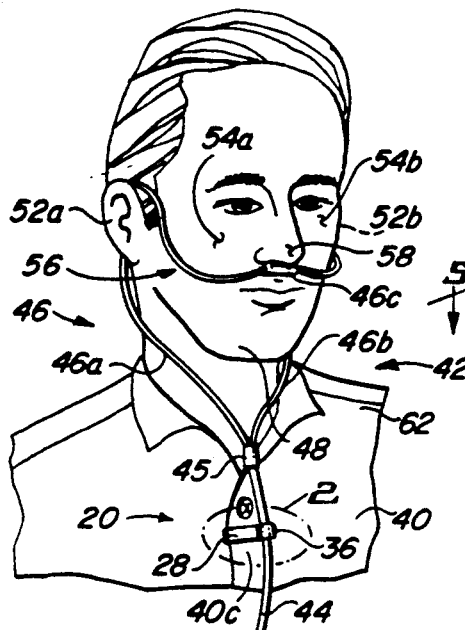
FIG. 1
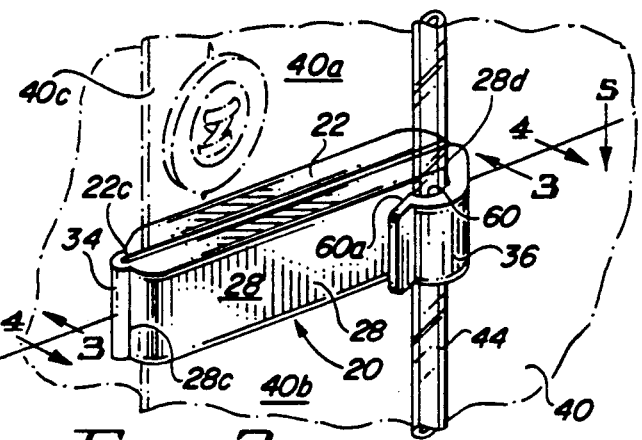
FIG. 2
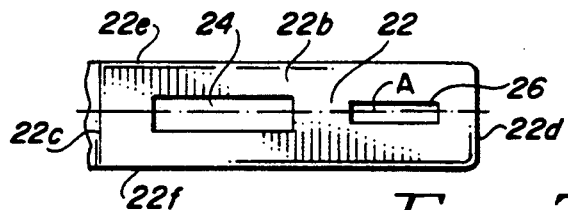
FIG. 3
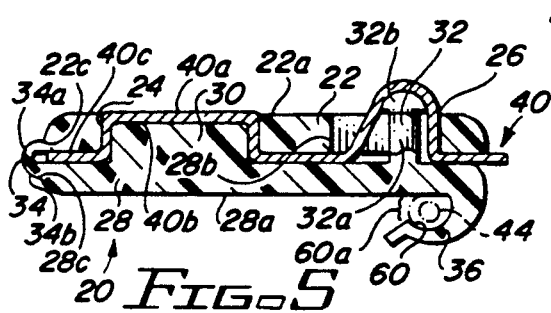
FIG. 5
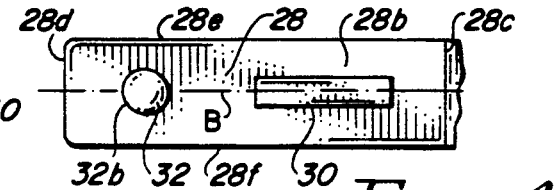
FIG. 4
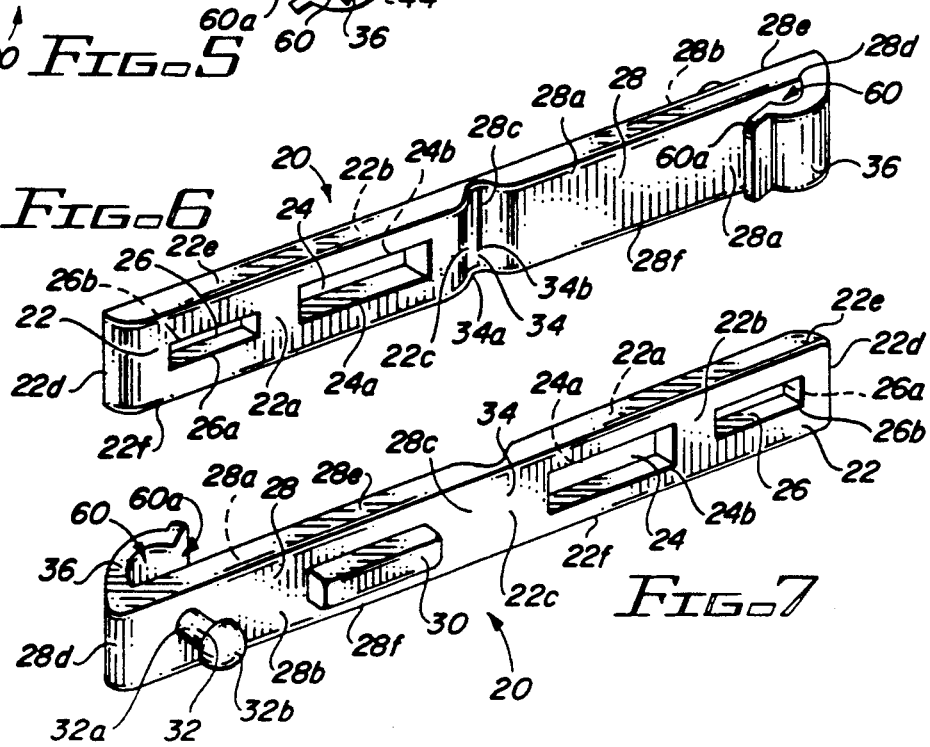
FIG. 6
FIG. 7

MEDICAL TUBE CLIP DEVICE

BACKGROUND OF THE INVENTION

1. Field of the Invention

The present invention generally relates to holders for medical tubing and, more particularly, is concerned with a medical tube clip device for use with oxygensupplying tubing and a cannula structure.

2. Description of the Prior Art

Medical advances in recent years have prompted the development of a variety of holders for various types of medical tubing. Formerly, such tubing was generally held in place on a patient's body by placement of strips of adhesive tape directly over the tubing onto the patient's body. For adjustment of the tubing, the adhesive strips would be removed and new strips applied to secure the adjusted tube in place. Such a process was quite painful for the patient since the skin was often irritated, bruised or torn by the adhesive tape. Additionally, the tape is easily contaminated by body fluids and not easily cleaned.

Therefore, a plurality of types of holders have been developed for use with particular types of medical tubing. Representative examples of such holders are disclosed in U.S. Pat. Nos. to Schlesinger (3,990,454), Johnson (4,165,748), Levine et al (4,170,995) and Eldridge, Jr. (4,336,806).

The Schlesinger and Johnson holders are designed particularly for use with catheters. Their purpose is to restrain the range of motion of the catheter such that the catheter is essentially immobilized relative to the patient's body. Such restraint thereby prevents the inadvertent withdrawal of the catheter from the patient's body.

The Levine et al holder may be utilized with a catheter, as well as with nasogastric and intravenous tubing. The Eldridge, Jr. holder is basically utilized during surgical operations for anchoring vacuum tubes, electrical cords and the like to a surgical drape on the patient.

Each of these holders has relatively simple features for anchoring a particular tube within the holder and for releasing the tube for necessary adjustment on the patient. Each holder has an adhesive-coated backing feature for adhering to the patient's skin, as with the Schlesinger, Johnson and Levine et al holders, or to a surgical drape, as with the Eldridge, Jr. holder.

None of these holders, however, sufficiently address the needs of a person who requires a continuous tubular intake of oxygen. This person may be a hospital patient confined to a bed or may be ambulatory, residing at home or in a nursing home or retirement center. In particular, the ambulatory person needs a medical tube holder which will securely anchor the oxygen-carrying tube to his or her garment. Such anchoring serves to prevent twisting of the tube and the cannula structure worn about the person's face so that the ambulatory person may pursue his or her daily routine of activities in comfort while receiving his or her necessary supply of oxygen. This anchoring device should have a feature for providing or distributing of the weight of the tubing over the person's body, particularly over the shoulders, so as to relieve the person's and neck from potential stress caused by the cannular structure.

None of the aforedescribed holders include these particular features. Consequently, a need exists for a medical tube holder specifically designed to meet the requirements for supplying oxygen to a hospital patient or ambulatory person.

SUMMARY OF THE INVENTION

The present invention provides a tube clip device designed to satisfy the aforementioned need by avoiding the drawbacks of the prior art without introducing other drawbacks. Instead, the clip device of the present invention provides expanded capabilities not available in the prior art devices.

One capability is the simplicity in design and construction of the clip device for inexpensive manufacture. A second capability is the simple latchability and releasability features of the clip device for ease in use by the person requiring the tubular intake of oxygen. A third capability is the stability of the clip device for preventing twisting of the oxygen-supply tube and for dispersing the weight of the tubing across the garment and upper torso of the person. Such capability ensures that the cannula structure attached to the tubing remains comfortably positioned around the person's face for continuous flow of oxygen to the person.

Accordingly, the present invention is directed to a tube clip device which comprises: (a) a flat base member having a plurality of bar slot and stud slot attachment elements extending therethrough between a pair of opposite surfaces of the base member; (b) a flat closure member having a plurality of bar and stud attachment elements merging and extending from one of a pair of opposite surfaces of the closure member, the bar and stud attachment elements being matable and interengageable with the bar slot and stud slot attachment elements of the base member for attaching the medical tube clip device to a garment of a person; (c) a living hinge pivotally connecting the base and closure members together for pivotal movement between opened and closed positions relative to one another; and (d) a clip element mounted on an outer surface of the closure member for releasably clasping a flexible medical tube supplying oxygen into a cannula structure for intake through the nostrils of a person.

The tube clip device is preferably molded in an integral one-piece construction and is made of a resiliently flexible material. The base and closure members are inserted over the inner and outer surfaces of the front edge of the person's garment, such as a shirt. The base and closure members are then pivoted by the living hinge to a closed position relative to one another, thereby enclosing the front edge of the garment therebetween. Completion of such closure movement aligns and then latches the bar slot and stud slot of the base member with the bar and stud of the closure member with the flexible fabric material of the garment therebetween, thereby attaching the tube clip device to the front edge of the garment enclosed therebetween.

The clip element mounted on the one opposite surface of the closure member is designed to releasably clasp or capture the flexible medical tube without significantly crushing or squeezing it. Yet the clip element is rigid enough to restrain the medical tube from twisting in either the right or left direction. The stability of the tube clip device as a whole serves to distribute or disperse the weight of the medical tube more or less evenly over the garment and upper torso of the person. Such restraint from twisting as well as distribution of weight of the medical tube relieves the cannula structure around the face from potential stress induced by these factors.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a perspective view of a tube clip device of the present invention, showing the device attached to a person's garment and clasping a medical tube for supplying oxygen to that person.

FIG. 2 is an enlarged perspective view of tube clip device encompassed by the circle 2 in FIG. 1.

FIG. 3 is a front elevational view of the base member of the tube clip device, as seen along line 3—3 of FIG. 2, showing the bar slot and stud slot attachment elements of the base member.

FIG. 4 is a rear elevational view of the closure member of the tube clip device, as seen along line 4—4 of FIG. 2, showing the stud and bar attachment elements of the closure member.

FIG. 5 is a longitudinal sectional view of the tube clip device of FIG. 2, taken along line 5—5, showing the base and closure members pivoted to a closed position and releasably latched to one another with a portion of flexible fabric material of the patient's garment disposed therebetween.

FIG. 6 is an enlarged perspective view of the tube clip device showing the outer sides of the base and closure members thereof interconnected by a living hinge and disposed in an opened position relative to one another.

FIG. 7 is another enlarged perspective view of the tube clip device after rotation 180° from its position of FIG. 6, showing the inner sides of the base and closure members and the living hinge interconnecting the members.

DETAILED DESCRIPTION OF THE INVENTION

Referring to the drawings and particularly to FIGS. 1 to 5, there is illustrated a medical tube clip device of the present invention, being generally designated 20. In its basic components, the tube clip device 20 includes a flat base member 22 having a plurality of attachment elements which at least include a bar slot 24 and a stud slot 26, and a flat closure member 28 having a plurality of attachment elements which at least include a bar 30 and a stud 32, best seen in FIGS. 3-5.

The tube clip device 20 further includes hinge means 34, preferably in the form of living hinge, pivotally connecting the base member 22 and closure member 24 together, and a clip element 36 mounted on an outer surface 28a of the closure member 28, as seen in FIGS. 2 and 5. The tube clip device 2-5 is releasably attachable to a garment 40 worn by a person 42. The clip element 36 mounted on the closure member 28 is capable of releasably clasping a flexible tube 44, such as a medical tube which is used for transmitting a substance such as oxygen to the person 42.

Referring particularly to FIG. 1, the flexible medical tube 44 is attached at one end (not shown) to an oxygen-supplying source (not shown). The medical tube 44 at the opposite end 44a is attached by a connector 45 in flow communication to a cannular 46 under the chin 48 of the person 42. Right and left cannula tubes 46a, 46b extend from the connector 45 upwardly around the right and left sides 50a, 50b respectively of the person's neck 50. The right and left cannula tubes 46a, 46b further extend upwardly behind and over the person's right and left ears 52a, 52b and then forwardly around right and left cheeks 54a, 54b of the person's face 56, terminating into a nasal cannular member 46c beneath the person's nose 58 which is then inserted into the nose 58.

Referring more particularly to FIGS. 3, 6 and 7, the flat base member 22 is generally rectangular in configuration, having oppositely facing planar surfaces 22a, 22b extending between pairs of opposite ends 22c, 22d and 22e, 22f. The bar slot 24 and stud slot 26 in the base member 22 are spaced from one another but generally aligned along the longitudinal centerline A of the base member 22. Both the bar slot 24 and stud slot are generally rectangular in configuration; however, the bar slot 24 is larger than the stud slot 26, being both wider and longer, as can be seen in FIG. 3. The bar slot 24 and stud slot 26 separately extend through the base member 22 between the oppositely facing outer and inner surfaces 22a, 22b thereof. The bar and stud slots 24, 26 have respective opposite open ends 24a, 24b and 26a, 26b on the opposite outer and inner surfaces 22a, 22b of the base member 22, as seen in FIGS. 6 and 7.

Referring now to FIGS. 4-7, the flat closure member 28 is generally rectangular in configuration and has oppositely facing planar surfaces 28a, 28b extending between pairs of opposite ends 28c, 28d and 28e, 28f. The bar 30 and stud 32 on the closure member 28 are spaced and shaped different from one another but generally aligned along the longitudinal centerline B of the closure member 28. The separate bar 30 and stud 32 protrude outwardly from the inner surface 28b of the closure member being opposite from outer surface 28a thereof mounting the clip element 36. The bar 30 and stud 32 of the closure member 28 are matable to and interengageable with the bar slot 24 and stud slot 26, respectively, in the base member 22 for attaching the tube clip device 20 to the garment 40, as seen in FIGS. 1, 2 and 5.

More particularly, the bar 30 is an elongated solid rectangular body being congruently receivable into the bar slot 24 of the base member 22. There is sufficient clearance or space between the bar 30 and wall portions of the bar slot 24 to accommodate the presence of portions of the flexible fabric material of the garment 40, as seen in FIG. 5. The stud 26 has a cylindrical stem portion 32a and an outer deformable head portion 32b attached to an outer end of the stem portion 32a and integrally formed therewith. The stem portion 32a is slightly smaller in cross-sectional width than the stud slot 26, thereby being congruently receivable into the stud slot 26. The deformable head portion 32b of the stud 32 is greater in diameter than the stud slot 26 such that the head portion 32b has to deform in shape to fit through the stud slot 26. On the other hand, once fitted through and past the stud slot 26, the head portion 32b will return to its original semi-spherical configuration and retain the base and closure members 22, 28 in the closed position, as seen in FIGS. 1, 2 and 5.

For releasably latching the stud 32 with the stud slot 26, the deformable head portion 32b of the stud 32 is pushed by the stem portion 32a through the stud slot 26 and outwardly therefrom at the open end 26a. Such action thereby latches the stud 32 against the stud slot 26 with opposite edge portions of the periphery of the head portion 32 overlying the outer surface 22a of the base member 22 adjacent to the opposite sides of the stud slot 26, preventing inadvertent or accidental withdrawal of the stud 32 from the stud slot 26.

Referring further to FIGS. 2 and 5-7, the base member 22 and closure member 28 are pivotally interconnected by hinge means 34, specifically denoted as a living hinge 34 in the preferred embodiment. The living hinge 34 has a strap-like configuration being narrower in width and thickness than both the base and closure members 22, 28. The living hinge 34 extends between and is integrally attached at opposite ends 34a, 34b to the ends 22c, 28c of the base and closure members 22, 28.

Referring to FIGS. 6 and 7, the one-piece tube clip device 20 is preferably molded such that the base and closure members 22, 28 and living hinge 34 are formed in the opened position. For attachment of the tube clip device 20 to the garment 40, the base and closure members 22, 28 are pivoted by the living hinge 34 towards the closed position of FIG. 5 for installation over the inner and outer surfaces 40a, 40b of the garment 40 at a front edge 40c thereof, as seen in FIGS. 1 and 2. The bar slot 24 and stud slot 26 of the base member 22 are interengaged with the bar 30 and stud 32 of the closure member 28, as hereinbefore described, so as to latch the base and closure members 22, 28 together in the closed position with the portion of the flexible fabric material of the garment 40 adjacent to the front edge 40c thereof clamped therebetween, as seen in FIG. 5. In such manner, the closed tube clip device 20 is firmly anchored to the garment 40, as seen in FIG. 1.

Referring to FIGS. 1, 2 and 5, the clip element 36 is mounted on the outer surface 28a of the closure member 28, adjacent to the one end 28d thereof. The clip element 34 has a generally hook-like configuration and defines an arcuate-shaped pocket 60 having an open side 60a and complementary in shape to the cross-section of the tube 44 to be clasped by the clip element 36. The open side 60a of the pocket 60 is narrower than the diameter of the tube 44 which requires squeezing of the tube 44 to insert it through the open side 60a and into the pocket 60. The pocket 60 of the clip element 36 could be of various sizes tailored to fit various diameters of the tube 44. The size of the pocket 60 and diameter of the tube 44 are sufficiently close so that the clip element 36 will secure the tube 44 therethrough without appreciably squeezing or crushing it so as to form a constriction therein but still grip the tube sufficiently to restrain it from twisting in either right or left directions relative to the clip element 36. Such restraint of the tube 44 is crucial for maintaining the cannula structure 46 comfortably around the ears 52a, 52b and face 56 of the person 42. Any twisting of the tube 44 can, in turn, cause twisting of the right and left cannula tubes 46a, 46b under the chin 48 of the person 42 such that the person 42 may experience (1) a choking sensation, and (2) a pulling sensation on the ears 52a, 52b and at the nose 58, which may result in skin irritation or infection. The positioning of the tube clip device 20 on the garment 40, as hereinbefore described, permits the garment 40 to serve as a further anchor for the tube 44 such that the weight of the tube 44 is dispersed more or less evenly over the garment 40. The shoulders 62 of the person 42 thereby assist in carrying the weight of the tube 44 as well.

The tube clip device 20, tube 44 and cannula structure 46 may be worn by a hospital patient confined to a bed or by an ambulatory person, residing at home or in a nursing home or retirement center. The ambulatory person is able to carry out a daily routine of activities as long as he or she receives the oxygen required. Therefore, the securement of the tube 44 and cannula structure 46 in their proper position on the person 42 is of paramount importance. The utilization of the medical tube clip device 20, as hereinbefore described, with the medical tube 44 and cannula structure 46 will attain these goals, permitting the ambulatory person 42 to function confortably in his or her daily life.

The medical tube clip device 20 is preferably of one-piece construction, being formed by use of conventional injection molding techniques and fabricated of a resilient flexible material, such as a suitable plastic. One example of a suitable plastic is acetate-Lexan. In one example, the base member 22 is about 1-¾ inches in length, ¾ inch in width and ⅛ inch in thickness. The cover member 24 is about the same size as the base member 22, but can be ¼ inch longer to enable easier disengaging of the base and cover members 22, 24 from one another. It should be pointed out that the term "medical" as used herein is not means as a limitation of the tube clip device 20 of the present invention but is used only for illustration purposes, since such application is but one, albeit a primary one, for the present invention.

It is thought that the present invention and its advantages will be understood from the foregoing description and it will be apparent that various changes may be made thereto without departing from its spirit and scope of the invention or sacrificing all of its material advantages, the form hereinbefore described being merely preferred or exemplary embodiment thereof.

I claim:

1. A tube clip device, comprising:
    (a) a flat base member having a pair of opposite surfaces and a plurality of first attachment elements, said first attachment elements including an elongated bar slot and an elongated stud slot being separate and spaced from one another and defined through said flat base member between and opening at said opposite surfaces of said flat base member, said bar slot being greater in length than said stud slot;
    (b) a flat closure member having a pair of opposite sides and a plurality of second attachment elements being matable and interengageable with said first attachment elements for attaching said device to a garment, said second attachment elements including an elongated bar and a cylindrical stud being separate, shaped different and spaced from one another and projecting outwardly from one of said opposite sides of said closure member;
    (c) means for pivotally connecting said base member and said closure member together for pivotal movement relative to one another between opened and closed positions; and
    (d) means mounted on the other of said opposite sides of said closure member for releasably clasping a flexible tube.

2. The clip device of claim 1 wherein said base member, closure member, connecting means and clasping means are integrally formed together in a one-piece construction and fabricated of a resiliently flexible material.

3. The clip device of claim 1 wherein said base and closure members are of substantially the same size and have generally rectangular configurations, each of said base and closure member including pairs of opposite edges and opposed flat planar surfaces extending between said edges.

4. The clip device of claim 1 wherein said bar slot and said stud slot have generally rectangular configurations.

5. The clip device of claim 4 wherein said bar of said closure member has a generally rectangular configuration being matable with said bar slot of said base member for releasably interengaging therein.

6. The clip device of claim 5 wherein said stud of said closure member has a generally cylindrical stem portion and a deformable head portion attached to and merging from an outer end of said stem portion, said head portion of said stud being greater in diameter than said stud slot of said base member.

7. The clip device of claim 6 wherein said head portion of said stud is deformable for extending through and outwardly from said stud slot of said base member such that said stud releasably latches with said stud slot with said stem portion of said stud extending through said stud slot of said base member.

8. The clip device of claim 1 wherein said means for pivotally connecting said base and closure members together is a strap-like living hinge narrower in width than said base and closure members, said hinge being integrally connected to said base and closure members and permitting pivotal movement of said base and closure members between opened and closed positions relative to one another.

9. The clip device of claim 8 wherein said base and closure members are fabricated in an opened position such that said living hinge is stressed when said base and closure members are pivoted to said closed position together.

10. The clip device of claim 9 wherein said bar and said stud of said closure member respectively releasably latch with said bar slot and said stud slot of said base member when said base and closure members are pivoted to said closed position relative to one another such that a portion of flexible fabric material of the garment is disposed in said bar slot and said stud slot between said base member and said bar and stud of said closure member.

11. The clip device of claim 1 wherein said clasping means is a clip element capable of releasably clasping a flexible tube.

12. A tube clip device, comprising:
(a) a flat base member being generally rectangular in configuration and having pairs of opposite ends and a pair of opposed planar surfaces extending between said ends, said base member also having an elongated bar slot and an elongated stud slot spaced from one another and of generally rectangular configurations, each extending separately through said base member between and opening at said opposed planar surfaces thereof, said bar slot being substantially greater in length than the stud slot;
(b) a flat closure member being generally rectangular in configuration and having pairs of opposite ends and a pair of opposed planar surfaces extending between said ends said closure member also having an elongated bar and a cylindrical stud spaced and shaped different from one another and merging and protruding outwardly from one of said planar surfaces of said closure member and being respectively matable and interengageable with said bar slot and said stud slot of said base member for securing a portion of flexible fabric material in said bar slot and stud slot between said base member and said bar and stud of said closure member for attaching said clip device to a garment, said stud of said closure member having a cylindrical stem portion and a deformable had portion attached to and merging from an outer end of said stem portion, said head portion of said stud being greater in diameter than said stud slot of said base member and being deformable for extending through and outwardly from said stud slot of said base member such that said stud releasably latches with said stud slot with said stem portion of said stud extending through said stud slot of said base member;
(c) a living hinge integrally and pivotally connecting said base member and said closure member together at one of said pairs of said opposite edges thereof for pivotal movement between opened and closed positions relative to one another; and
(d) a clip element mounted on an outer side of said closure member opposite from said base member in said closed position, said clip element being capable of releasably clasping a flexible tube.

13. The clip device of claim 12 wherein said base member, closure member, connecting means and clasping means are integrally formed together in a one-piece construction and fabricated of a resiliently flexible material.

14. The clip device of claim 12 wherein said bar slot and said stud slot have generally rectangular configurations.

15. The clip device of claim 12 wherein said living hinge is a strap-like hinge narrower in width than said base and closure members.

16. The clip device of claim 14 wherein said clip element has a generally hook-like configuration and defines an arcuate-shaped side-opening pocket being complementary in shape to the cross-section of the tube to be clasped by said clip element.

17. The clip device of claim 12 wherein said base and closure members are fabricated in said opened position such that said living hinge is stressed when said base and closure members are pivoted to said closed position together.

* * * * *